(12) United States Patent
Barak et al.

(10) Patent No.: US 10,209,206 B2
(45) Date of Patent: Feb. 19, 2019

(54) METHOD AND SYSTEM FOR DETERMINING STRAIN DISTRIBUTION IN A SAMPLE

(71) Applicant: NOVA MEASURING INSTRUMENTS LTD., Rehovot (IL)

(72) Inventors: Gilad Barak, Rehovot (IL); Shay Wolfling, Kiryat Ono (IL); Cornel Bozdog, San Jose, CA (US); Matthew Sendelbach, Fishkill, NY (US)

(73) Assignee: NOVA MEASURING INSTRUMENTS LTD., Rehovot (IL)

( * ) Notice: Subject to any disclaimer, the term of this patent is extended or adjusted under 35 U.S.C. 154(b) by 291 days.

(21) Appl. No.: 14/903,629

(22) PCT Filed: Jul. 8, 2014

(86) PCT No.: PCT/IL2014/050615
§ 371 (c)(1),
(2) Date: Jan. 8, 2016

(87) PCT Pub. No.: WO2015/004662
PCT Pub. Date: Jan. 15, 2015

(65) Prior Publication Data
US 2016/0139065 A1    May 19, 2016

Related U.S. Application Data

(60) Provisional application No. 61/843,478, filed on Jul. 8, 2013.

(51) Int. Cl.
*G01N 23/00* (2006.01)
*G01N 23/20* (2018.01)
*G01L 1/24* (2006.01)

(52) U.S. Cl.
CPC ............... *G01N 23/20* (2013.01); *G01L 1/24* (2013.01); *G01N 2223/607* (2013.01); *G01N 2223/611* (2013.01)

(58) Field of Classification Search
CPC ..... G01L 1/24; G01N 2223/607; G01N 23/20
See application file for complete search history.

(56) References Cited

U.S. PATENT DOCUMENTS

| 5,828,724 A | 10/1998 | Kurtz | |
|---|---|---|---|
| 7,838,309 B1 * | 11/2010 | Wack | G01B 11/16 257/288 |

(Continued)

FOREIGN PATENT DOCUMENTS

WO    2013169791 A1    11/2013

OTHER PUBLICATIONS

International Searching Report, dated Nov. 9, 2014. In corresponding application No. PCT/IL2014050615.

*Primary Examiner* — Dani Fox
(74) *Attorney, Agent, or Firm* — Browdy and Neimark, PLLC (57) ABSTRACT

A control system is presented for use in measuring one or more parameters of a sample. The control system comprises an input utility and a processor utility. The input utility is configured for receiving input data including first data comprising X-ray Diffraction or High-Resolution X-ray Diffraction (XRD) response data of the sample indicative of a material distribution in the sample, and second data comprising optical response data of the sample to incident light indicative of at least a geometry of the sample. The processor utility is configured and operable for processing and analyzing one of the first and second data for optimizing the other one of the first and second data, and utilizing the (Continued)

optimized data for determining said one or more parameters of the sample including a strain distribution in the sample.

14 Claims, 6 Drawing Sheets

(56) References Cited

U.S. PATENT DOCUMENTS

| | | |
|---|---|---|
| 8,437,450 B2 | 5/2013 | Wall et al. |
| 2009/0279090 A1 | 11/2009 | Wolf et al. |
| 2013/0208973 A1 | 8/2013 | Brill |

* cited by examiner

XX component of stress tensor ($\sigma_{xx}$) after source and drain formation in strained-silicon PMOS transistor; distances are micrometers

METHOD AND SYSTEM FOR DETERMINING STRAIN DISTRIBUTION IN A SAMPLE

TECHNOLOGICAL FIELD AND BACKGROUND

The present invention is in the field of measurement techniques for measuring various properties/parameters of samples, and relates to a measurement method and system particularly useful for determining strain distribution in a sample, such as a semiconductor structure.

Various optical measurement techniques have been developed for measuring the strain and other properties of a material.

For example, U.S. Pat. No. 8,437,450 describes a method for analysis including directing a converging beam of X-rays toward a surface of a sample having multiple single-crystal layers, including at least a first layer and a second layer that is formed over and tilted relative to the first layer. The X-rays that are diffracted from each of the first and second layers are sensed simultaneously while resolving the sensed X-rays as a function of angle so as to generate a diffraction spectrum including at least a first diffraction peak due to the first layer and a second diffraction peak due to the second layer. The diffraction spectrum is analyzed so as to identify a characteristic of at least the second layer. This technique enables determination of average strain and relative material concentrations.

The ongoing progress of semiconductor technology leads to shrinking device dimensions as well as more complex device designs. Characterization of modern semiconductor devices presents an incredibly challenging task, requiring suitable metrology tools, which are critical for the continual process of this development.

Several metrology technologies have been developed for semiconductor device characterization. Examples are CD-SEM, utilizing the high resolution allowed by electron microscopy, and Optical Critical Dimension (OCD) metrology.

GENERAL DESCRIPTION

There is a constant and growing need for novel approach for optimizing determination of various parameters of a sample, e.g. determining strain distribution in a sample, enabling to improve metrology capabilities.

The present invention provides a novel measurement technique, which, in some embodiments, is aimed at optimizing X-ray Diffraction or High-Resolution X-ray Diffraction (both termed herein as "XRD") measurements by information about the geometrical parameters of the sample's structure, e.g. pattern features, as well as vice versa: using the XRD measured data for optimizing/interpreting a different geometry-related measurement, thereby enabling determination of both the sample geometry and materials properties/compositions. The geometry-related data may be provided by a different measurement technique, such as in optical measurements, e.g. Optical Critical Dimensions (OCD) measurements, CD-AFM, CD-SEM, as well as other X-ray techniques, etc.

Thus according to some aspects of the present invention, it provides a method and system for use in determining one or more parameters of a sample (e.g. strain distribution in a sample/material) based on the geometrical constraints imposed on the materials available from external data sources and vice versa. A multitude of possible geometries can be available, and for each geometry the strain distribution can be obtained.

According to some other aspects of the invention, it provides a novel technique for solving the inverse problem for an XRD measurement. In some embodiments of the invention, this is achieved by combining information on geometry and material strain in order to calculate spectral lineshapes, optimize the best lineshape match to measured data and extract the most probable geometry and strain, and/or by adding external information on geometry from structure design, and/or, as indicated above, by adding external information on geometry from another measurement such as OCD, CD-AFM, CD-SEM or another XR technique, and/or by combining spectra and/or results from multiple toolsets including an XRD system with the purpose of imposing physical and material constraints and reducing the degree of uncertainty of the extracted results.

The present invention also provides for simultaneously solving the inverse problem for an XRD measurement and optical measurement of the same sample/structure by imposing the constraint that both measurements arise from the same geometrical and material model.

Further, the invented approach for solving the inverse problem for an XRD measurement is based on minimizing a global merit function (MF) as a combination of the individual merit functions of two or more toolsets for a given measurement of a structure.

The principles of the present invention are based on the inventors' understanding of the key levels of complexity for XRD-based signal analysis. The target use of common XRD metrology, in its simplest configuration is based on the identification of XRD peak locations and intensities, which allows for the derivation of average strain and relative material concentrations. A more complex task of identifying the XRD peak profile/shape (referred to herein as "lineshapes") utilizes a single trace of one or more XRD peaks, which provides for extracting more than just the peak position and height (as in the previous case). By extracting the peak shape, one can learn on the sample properties. However, this is often the case that this XRD lineshape measurement technique is incapable of determining the sample properties with desired accuracy because different samples are characterized by very similar XRD peak profiles. Yet further measurement techniques, so-called Critical Dimension Small Angle X-ray Scattering (CD-SAXS) and Reciprocal Space Mapping (RSM) techniques, which can be used to provide a full 2D XRD scan around diffraction peak\s with very high sensitivity and resolution. Although these measurement techniques provide extensive information on the sample structure, they are very (possibly prohibitively) slow for in-line metrology.

The present invention proposes a new approach for determination of various properties of a sample from XRD measurements being optimized by geometric data about the sample and/or from optical or other geometry-based measurements optimized by XRD measured data. The technique of the present invention provides for obtaining the strain distribution in a material or sample from the sample geometry and materials, as well as obtaining the distribution of XRD intensity vs. angle of sample with respect to source and detector (lineshape) from the sample materials and strain distribution in the material.

The present invention provides for determining the sample geometry and strain distribution from the measured XRD lineshape and Scatterometry (Optical CD or OCD) data. As indicated above, in some embodiments, the OCD or other external source geometry-related data is not needed, as the basic algorithm is an "inverse problem" solver that finds the geometry and/or material properties including strain by optimizing the match between a calculated spectral response and the measured one. OCD or other external source data can contribute with additional information on the measured sample, or with additional constraints to the XR optimization model, or can be simultaneously solved together with the XR data (possibly in a "hybrid metrology" embodiment). OCD data can be neglected altogether; in such embodiment the sample geometry and strain distribution would be extracted only from XRD modeling.

Thus, according to one broad aspect of the invention, there is provided a control system for use in measuring one or more parameters of a sample, the control system comprising:

(a) an input utility for receiving input data including first data comprising X-ray Diffraction or High-Resolution X-ray Diffraction response data of the sample indicative of material distribution in the sample, and second data comprising optical response data of the sample to incident light indicative of at least a geometry of the sample;

(b) a processor utility configured and operable for processing and analyzing one of the first and second data for optimizing the other one of the first and second data, and utilizing the optimized data for determining said one or more parameters of the sample including a strain distribution in the sample.

In some embodiments, the second data is further indicative of material properties of the sample.

In some embodiments, the second data further includes data indicative of a different X-ray measurement.

The second data indicative of the optical response of the sample to incident light may include measured data indicative of pattern features in the sample. Such measured data may be indicative of at least one of the following: Optical Critical Dimension (OCD) measurement, CD-AFM measurement, CD-SEM measurement.

In some embodiments, the first data includes data indicative of a profile of at least one XRD spectral peak, and the second data includes data indicative of at least one spectral response of the sample.

In some embodiments, the processor utility comprises:

a calculation engine module configured and operable for receiving data indicative of the material structure and geometry of a sample and determining a spectral profile for an XRD peak in and XRD response of the sample;

a fitting module for analyzing said first and second data and the determined profile for the XRD peak, optimizing a best match between the determined spectral profile and the first data, and a sample parameter calculator module for analyzing the best match data and extracting optimal second data for the geometry and strain distribution of the sample.

According to another aspect of the invention, there is provided a measurement system for measuring one or more parameters of a sample. The measurement system comprises:

first and second units for providing first and second data comprising respectively X-ray Diffraction or High-Resolution X-ray Diffraction (XRD) response data of the sample indicative of a material distribution in the sample and optical response data of the sample to incident light indicative of at least a geometry of the sample; and the above described control system, configured for communicating with the first and second units and operable for processing and analyzing one of the first and second data for optimizing the other one of the first and second data, and utilizing the optimized data for determining said one or more parameters of the sample including a strain distribution in the sample.

In some embodiments, the first unit comprises a measuring device for performing X-ray Diffraction or High-Resolution X-ray Diffraction measurement on the sample and providing the first data indicative of the material structure of the sample. The second unit may comprise an optical measuring device for performing optical measurement on the sample and providing the second data indicative of the geometry of the sample.

In some embodiments, at least one of the first and second units comprises a storage device for storing the at least one of the first and second data, and the other one of the first and second units comprises a measuring unit for performing measurements on the sample and providing the other one of the first and second data. In some embodiments, both the first and second units are memory utilities of a storage system for storing the first and second data.

According to yet another broad aspect of the invention, there is provided a method for use in measuring one or more parameters of a sample, the method comprising:

providing first and second data comprising respectively X-ray Diffraction or High-Resolution X-ray Diffraction response data of the sample indicative of a material distribution in the sample and optical response data of the sample to incident light indicative of a geometry of the sample; and processing and analyzing one of the first and second data for optimizing the other one of the first and second data, and utilizing the optimized data for determining said one or more parameters of the sample including a strain distribution in the sample.

In some embodiments, the processing comprises combining first and second data indicative of the material structure and geometry for determining a spectral profile for an XRD peak, optimizing a best match between the determined spectral profile and measured first data, and extracting optimal data for the geometry and strain distribution of the sample.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 4 and 5A-5D show a non-limiting example of the method according to the invention, where

DETAILED DESCRIPTION OF EMBODIMENTS

As indicated above, the present invention, in some embodiments thereof, provides for using geometry-related data (e.g. reference data or measured data), e.g. from optical measurements (OCD measurements), for optimizing XRD measurements, and/or using XRD measured data, indicative of material distribution in the sample, for optimizing other measurement technique for measuring geometric parameters of the sample, as well as material properties of the sample.

Figure 1A:
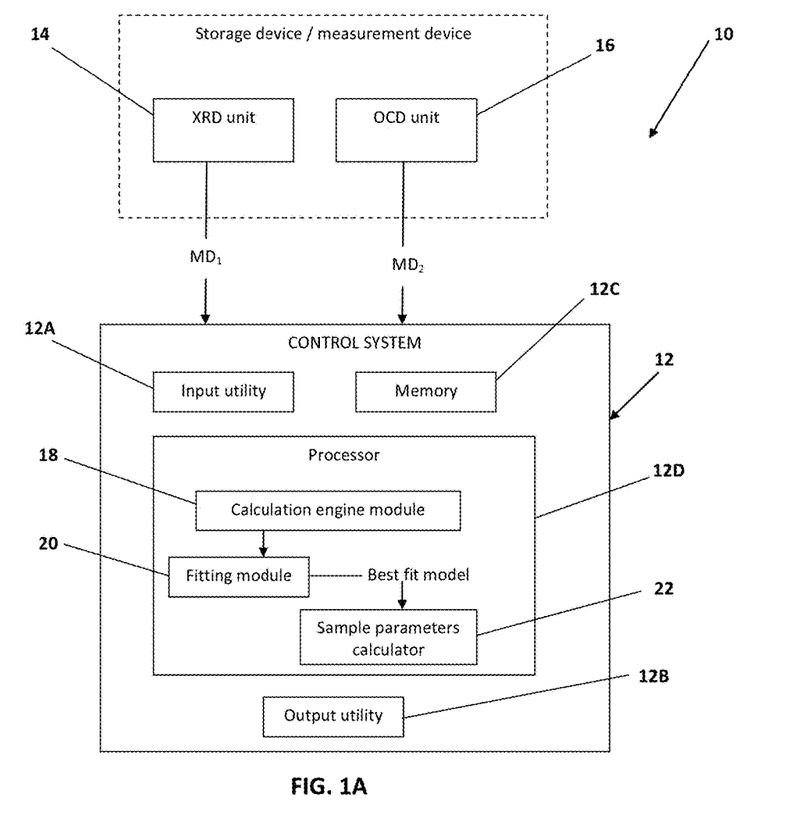
FIG. 1A is a block diagram of an example of a measurement system utilizing a control system of the present invention for use in measuring sample's parameters(s) such as strain distribution in a sample.

Referring to FIG. 1A, there is illustrated, by way of a block diagram, a measurement system 10 utilizing a control system 12 configured and operable according to the present invention for processing and analyzing measured for determining strain distribution in a sample. The measurement system 10 includes an XRD unit 14 and OCD unit 16 providing respectively XRD and OCD measured data $MD_1$ and $MD_2$.

It should be understood that OCD unit 16 actually presents an external data source unit providing geometry-related data about a sample, which is either the same sample or a sample similar to that for which the XRD data is being provided. As described above, the geometry-related data may be pre-stored reference data, a prior known from the structure design, or may be provided as external information from another measurement such as OCD, CD-AFM, CD-SEM or another XR technique.

It should also be understood that either one or both of XRD and OCD units 14 and 16 may be constituted by the respective measurement unit(s) carrying out the measurements on the same sample, or may be constituted by storage utilities (e.g. of the same or different storage device) where the XRD and OCD measured data is/are stored. The control system 12 of the invention is configured as a computer system including inter alia data input and output utilities 12A and 12B, memory utility 12C, and a processor utility 12D. The control system 12 is configured for data communication with the XRD and OCD units using any known suitable communication technique, e.g. wireless communication, via a communication network.

For example, the control system 12 receives input data including the XRD measured data $MD_1$ and the other (e.g. OCD) measured data $MD_2$ which are indicative of respectively material distribution in the sample and geometry (and possibly also material properties) of the sample under measurements. The processor utility 12D operates to use the geometry-related measured data $MD_2$ for interpreting the XRD material-related measured data $MD_1$ or using the XRD material-related measured data $MD_1$ for interpreting the use the geometry-related measured data $MD_2$, and possibly also optimizing both of these measured data pieces for improving measurements of various parameters of the sample.

It should be noted that the control system 12 of the invention can be used in a so-called on-line mode, when XRD and OCD data are directly provided from the respective measurement devices during the measurement session. In this connection, the following should be noted. XRD is a relatively slow measurement method compared to OCD. Accordingly, information from the relatively fast OCD metrology tool may be used to identify when the process starts deviating from its nominal performance, and only then trigger an XRD measurement to better identify the nature of this deviation. Such approach could significantly reduce the throughput overhead involved in the XRD measurements.

Figure 1B:
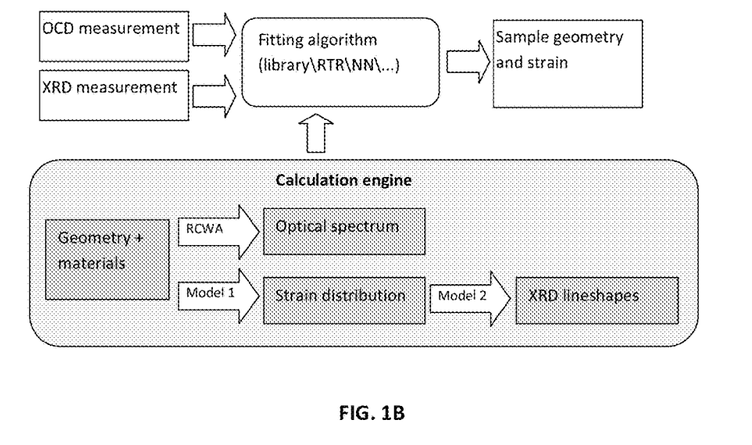
FIG. 1B is a flow diagram of an example of the operation of the control system of FIG. 1A.

FIG. 1B illustrates a flow diagram of an example of the operation of the control system 12. In the present example, the geometry-related data is constituted by OCD measured data. As shown, XRD and OCD data pieces $MD_1$ and $MD_1$ are input into a fitting utility 20 of the processor 12D, which is operated by a calculation engine module 18 to run one or more suitable fitting algorithms, and then the best fit model is used by a sample parameters calculator module 22 to determine one or more parameters of the sample.

The calculation engine module operates to solve an inverse problem. More specifically, it processes the geometry and materials related data about the sample using suitable algorithms (e.g. RCWA and Model 1 processing as will be described below) to simulate theoretical data indicative of geometric parameters (e.g. optical spectrum/signature) and simulate theoretical data indicative of the sample's material structure/material distribution (e.g. strain distribution). Then, the simulated strain distribution is analyzed using Model 2 processing (as will be described further below) to determine a suitable/corresponding XRD data (XRD lineshape). The latter is used in the modeling/fitting process to determine the sample geometry and strain for the specific sample.

Figure 2:
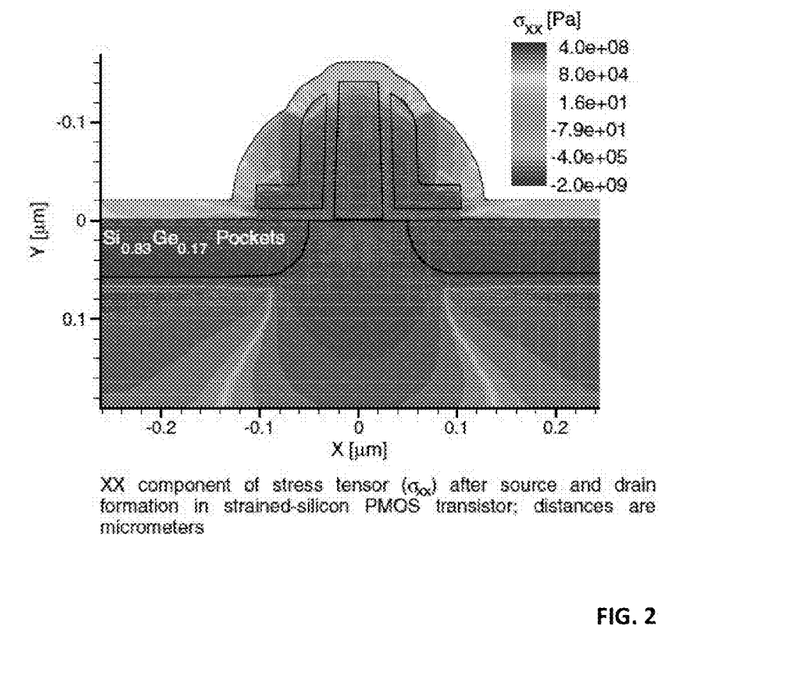
FIG. 2 illustrates calculated stress distribution in strained-Si CMOS device, using Synopsis SW.

In general, strain distribution in a sample can be determined for the sample of given geometry and materials distribution using a suitable model-based algorithm (termed to herein as "Model 1"). This is a standard problem in elasticity. Specifically, for applications in the field of semiconductors, the importance of stress distributions for actual device performance led to development of several modeling tools already available in the market (such as from Synopsis, Mentor Graphics, Cadence etc.). In this connection, reference is made to FIG. 2 illustrating calculated stress distribution in strained-Si CMOS device, using Synopsis SW. In the figure, the XX-component of stress tensor $\sigma_{xx}$ is shown after source and drain formation in strained-silicon PMOS transistor (distances are in micrometers).

This problem is made more complicated by the fact that relaxation mechanisms (e.g. dislocations) may have a strong effect on strain, but a negligible effect on geometry. Using such tools, given sample geometry and materials, one should be able to either directly deduce the strain map, or at least put strong restrictions on the possible strain distribution.

Figure 3A:
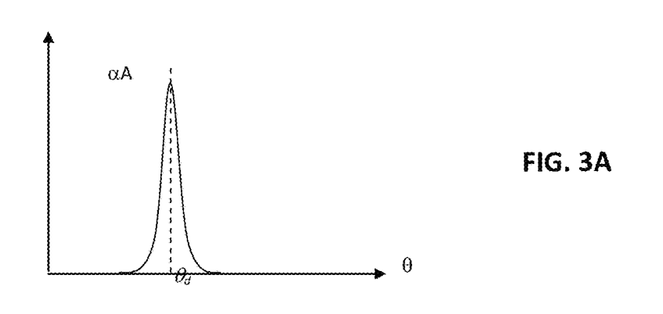
FIG. 3A shows a schematic XRD peak amplitude vs. angle for homogeneous-stress sample.

In order to consider derivation of XRD lineshape (profile) from the materials and strain distribution (referred to herein as "Model 2"), the effects of the sample geometrical structure can be neglected, and only the distribution of interatomic distances can be considered, which is directly derivable from the strain distribution. Then, the following approach can be used: One or more XRD peaks of interest can be chosen from the XRD data, where each XRD peak is related to a different material and crystal plane. The choice of XRD peak(s) for analysis is based on the application and sample's parameters of interest. Such peaks in the XRD spectrum arise from interaction of X-ray radiation with the specific materials. Based on the modeling tool described above (Model 1), the strain distribution for each specific material can be found. The expected XRD lineshape (profile/shape of the XRD peak) is then derived from the strain distribution. Then, the following can be done:

A constant strain S can be considered, leading to interatomic distance d in the measured crystal plane. This distance would dictate an XRD peak-location $\theta_d$, with amplitude proportional to the amount of such atoms A. This is exemplified in FIG. 3A showing a schematic XRD peak amplitude vs. angle for homogeneous-stress sample. The lineshape/profile of such peak has some width, dictated (mainly) by the characteristics of the XRD measuring tool. The area of the peak is determined by A. Considering the width is application-independent (determined by the tool), the peak height is given by αA. This is termed lineshape/profile:

$$I = \alpha A \cdot P(\theta - \theta_d).$$

Here, $P(\theta)$ is the peak functional form, and it is shifted to be centered on $\theta_d$.

Considering a distribution of such regions, where each region is characterized by slightly different strain $S_i$, interatomic distance $d_i$ and relative abundance $A_i$, each region will create a peak at $\theta_i$. The measured intensity will be (to first approximation) given by the sum over all the corresponding diffraction peaks $$I(\theta) = \sum_i \alpha A_i \cdot P(\theta - \theta_i).$$

Writing this for continuous strain distribution, gives:

$$I(\theta) = \int \alpha A_i \cdot P(\theta - \theta_i) di,$$

which is the convolution of the strain distribution $A_i$ and the tool 'ideal XRD peak' lineshape $P(\theta)$. Since the tool ideal lineshape can be characterized, it can be de-convolved from the measurement. Alternatively, if the peak width is significantly smaller than the width of the distribution $A_i$, it can be approximated to a δfunction, in which case the XRD amplitude $I(\theta_i)$ provides a direct measure of the relative abundance of strain $S_i$ in the sample.

Figure 3B:
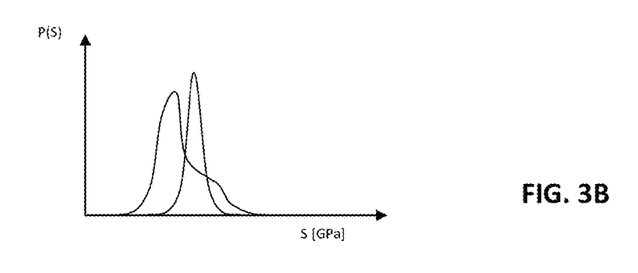
FIG. 3B shows stress distribution extracted from an XRD peak lineshape measurement.
Figure 4:
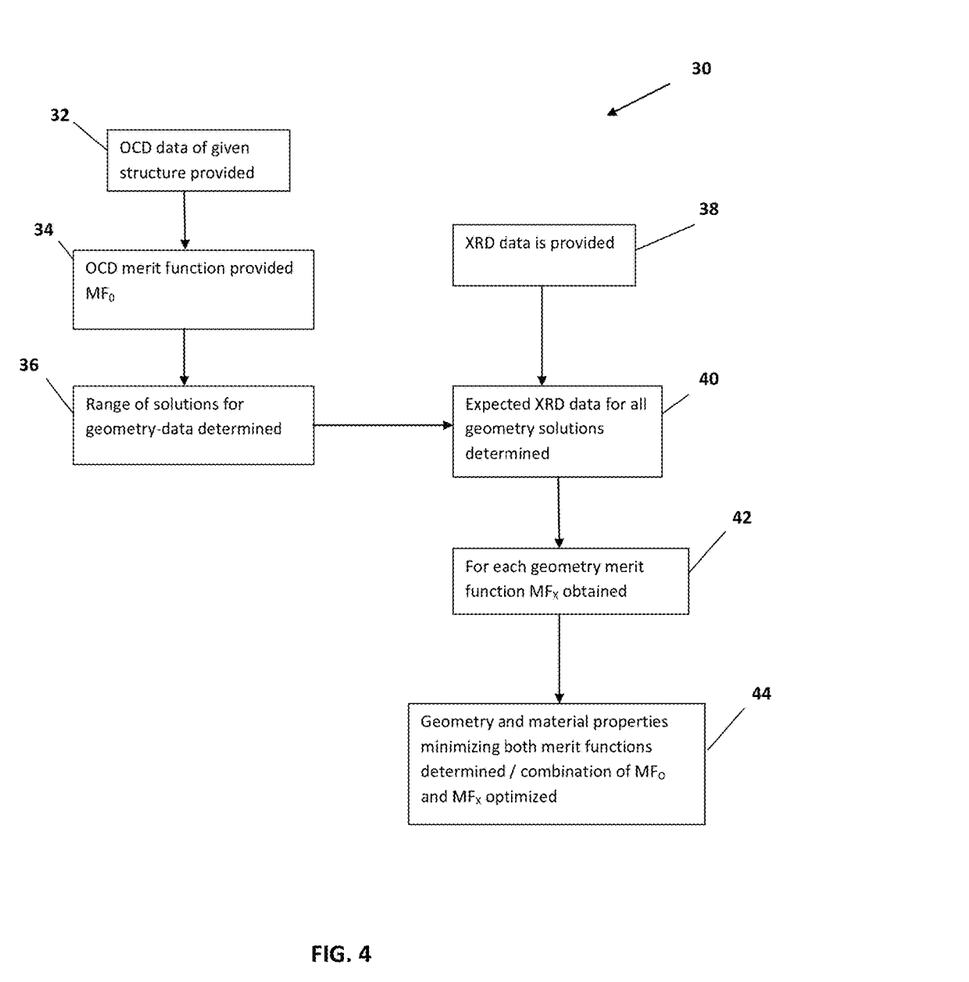
FIG. 4 is a flow diagram of the main steps in this method and FIGS. 5A-5D show examples for measured/simulated data pieces.

Consequently, the result of an XRD measurement, implementing such interpretation approach, is the stress distribution in the probed material. FIG. 3B shows such stress distribution as could be extracted from an XRD peak lineshape measurement.

As described above the present invention also provides for integrating the XRD and OCD data. To this end, in addition to the method described above, the XRD data can be further augmented and hybridized by OCD data (e.g. information from Optical CD measurements).

As described, an XRD measurement provides some information on the strain and material distribution in the sample. OCD provides information on the sample geometry, which can be related to strain and material information through modeling. Consequently, these channels provide correlated information, which can be concurrently used to improve and stabilize the metrology (they can of course also be used separately)

The following is a non-limiting example for integration of these information channels. The eventual optimized method can be improved based on better characterization of the uncertainties and information quality of the different channels.

Figure 5A:
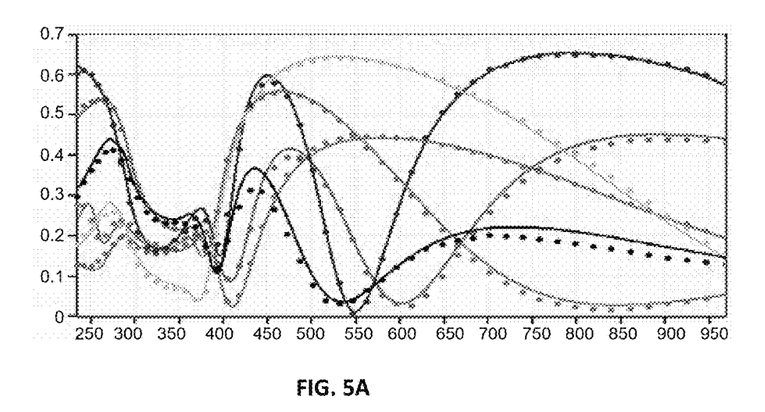

In this connection, reference is made to FIGS. 4 and 5A-5D exemplifying a flow diagram 30 of such method and examples for measured data pieces. In this example, OCD measured data of a given structure is provided (step 32). FIG. 5A shows measured OCD spectra presented here by solid-line graphs, and fitted theoretical data shown by dotted graphs, where several spectra (graphs) correspond to different measurement channels (polarizations, AOIs, azimuths, etc.).

Figure 5B:
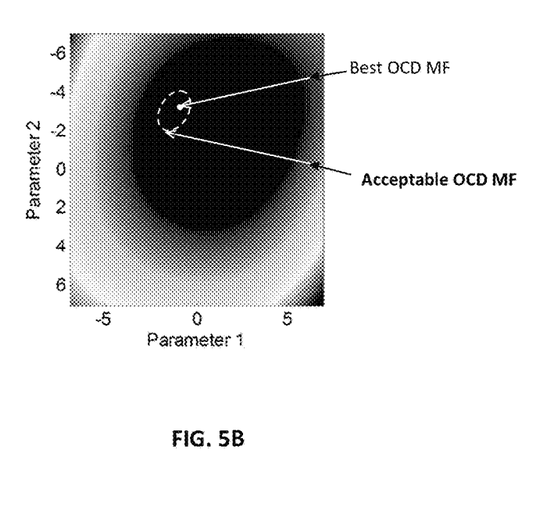

Based on the OCD data, an 'OCD merit function' $MF_O$ can be determined to any sample geometry (step 34), by quantifying the degree of matching between a calculated and the measured spectral response. Standard OCD solution to the inverse problem is based on finding the geometry which yields the best $MF_O$. Hence, a range of such possible solutions can be identified, all with 'acceptable' $MF_O$s (step 36). Schematic interpretation result for OCD data is presented in FIG. 5B, assuming two parameters of interest. Using the measured spectra and the OCD interpretation engine, it is possible to assign different 'merit functions' to different combinations of geometric sample parameters.

Figure 5C:
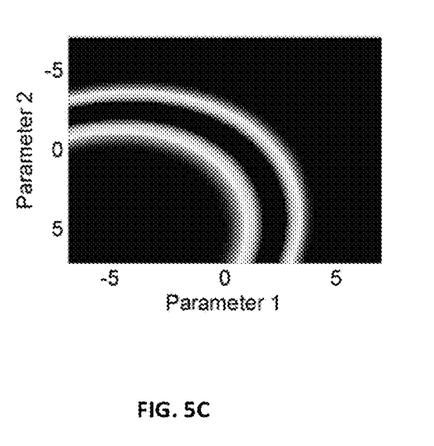

An XRD measurement is taken (step 38), which upon analysis provides a stress distribution. This is exemplified in FIG. 5C, showing schematic interpretation result for XRD lineshape.

Using the deduce stress distribution and the calculation engine relating geometry and stress, it is possible to assign different 'merit functions' to different combinations of geometric sample parameters.

Figure 5D:
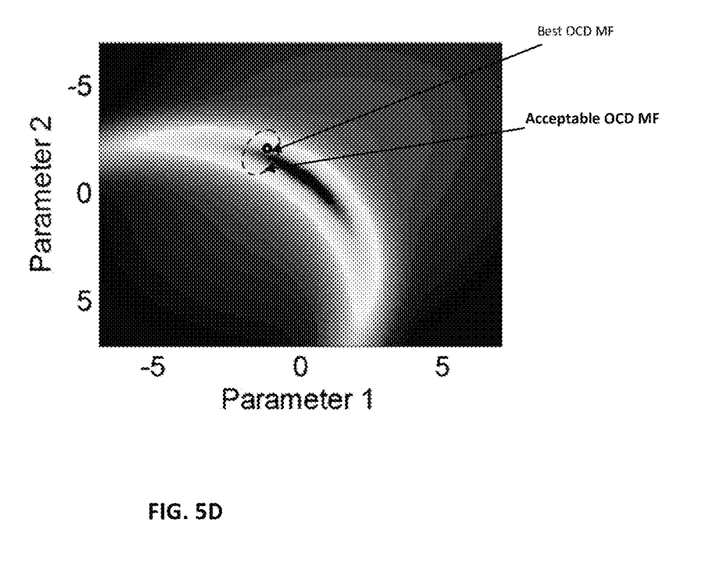

As described above, the expected XRD signal can be calculated for all geometries in this range of OCD possible solutions, or it can be found how probable it is that this geometry gives rise to the measured XRD signal (step 40). Consequently, another merit function $MF_X$ can be obtained for each geometry (step 42). Ideally, the geometry and material properties parameters can be found that minimize both merit functions. In practice, this might not be the case (partly due to imperfections in the models and neglected influences of weaker parameters), and concurrent optimization can improve the result by optimizing a combination of $MF_O$ and $MF_X$ (step 44). An example for such 'combined MF' (corresponding to the example presented in FIGS. 5B and 5C) is presented in FIG. 5D showing schematic combined interpretation result for XRD and OCD. Using both XRD and OCD information, a combination of parameters is found which both suit the OCD and the XRD measurements.

Specifically, $MF_O$ and $MF_X$ will have different sensitivities and suffer differently from correlations for different layout parameters. Correspondingly, such concurrent optimization can include different selection of fixed\floating parameters (and possibly even simple injection of parameters). Such concurrent optimization can use an existing Hybridization approach already described elsewhere (see e.g. US 2013/0208973 assigned to the assignee of the present application and incorporated herein by reference).

The methods and implementations described above can be further expanded. For example, multiple hybridization approach can be used according to which information from other metrology tools (such as CD-SEM, TEM, AFM, Raman spectroscopy etc.) is similarly integrated into the fitting procedure. While some of these metrology sources could provide additional information on the sample geometry (e.g. CD-SEM), others may work to stabilize and verify the stress and composition distribution (e.g. Raman spectroscopy).

Also, X-ray reflectivity (XRR) measurements, taken at extremely oblique angles, may be used to provide accurate and reliable information on thin thicknesses. When measuring a patterned structure, this method can measure thicknesses of horizontal layers. This information can then be input into the geometry interpretation algorithm, and further stabilize the OCD metrology. One advantage of XRR in this context is that it may be possible to use the same X-ray tool to measure both XRD and XRR.

Further, residue detection may be used. Identification of residual material, which was not fully removed by a previous fabrication process (e.g. CMP, etch), is one of common parameters of interest in OCD applications. The remaining layers in such cases may be very thin, and have small impact on the optical reflection signal. However, since XRD provides clear separation between different materials, a residue layer may be easily identifiable, providing clear input for an otherwise-weak parameter in the OCD interpretation.

As an alternative to the previous option, it is possible to use the (fast) OCD measurement to identify whether a site is suspected as suffering from remaining residues, and pass suspected sites to the (slow) XRD measurement head, for verification.

The analysis presented above can be applied to measurements of RSM/CD-SAXS, instead or in addition to XRD, enabling to obtain a full 2D XRD scan around diffraction peak\s. The proposed measurement and analysis flow remains the same, while the theoretical spectrum response reconstruction and measurement matching is specific RSM/CD-SAXS.

Also, as stated, the approach of the invention described above allows concurrent use of XRD measurement information and OCD (or other) metrology. The proposed methodology, involving the definition of two 'merit functions' (one for each metrology method) is only one of the possible algorithmic approaches to interpret the measured data. Alternative options involve defining a single merit function which could integrate the different information sources in highly nontrivial (e.g. nonlinear) ways.

As indicated above, XRD is a relatively slow measurement method (e.g. compared to OCD), often requiring many seconds or even minutes for a high-quality measurement. The resulting throughput hit would limit the applicability of the proposed method. A mitigation to this issue could be different sampling (across wafer or within wafers) for the XRD and the other metrology. An extension of this idea is to use information from the 'fast' (OCD) metrology to identify when the process starts deviating from its nominal performance, and only then trigger an XRD measurement to better identify the nature of this deviation. Such approach could significantly reduce the throughput overhead involved in the XRD measurements.

The invention claimed is:

1. A control system for use in measuring one or more parameters of a sample, the control system comprising:
    (a) an input utility for receiving input data including first data comprising X-ray Diffraction or High-Resolution X-ray Diffraction (XRD) response data of the sample indicative of a material distribution in the sample, and second data comprising optical response data of the sample to incident light indicative of at least a geometry-related data of a sample, being either the same sample or a sample similar to said sample for which the XRD data is received;
    (b) a processor utility configured and operable to utilize the second data for processing and analyzing said first data for optimizing the first data, and utilizing the optimized first data for determining said one or more parameters of the sample including a strain distribution in the sample.

2. The control system of claim 1, wherein the second data further includes data indicative of a different X-ray measurement.

3. The control system of claim 1, wherein the second data is further indicative of material properties of the sample.

4. The control system of claim 1, wherein said second data comprises data indicative of optical response of the sample to incident light and includes optical measured data indicative of pattern features in the sample.

5. The control system of claim 4, wherein said optical measured data is indicative of at least one of the following: Optical Critical Dimension (OCD) measurement, CD-AFM measurement, CD-SEM measurement.

6. The control system of claim 1, wherein said first data includes data indicative of a profile of at least one XRD spectral peak, and the second data includes data indicative of at least one spectral response of the sample.

7. The control system of claim 3, wherein the processor utility comprises:
    a calculation engine module configured and operable for receiving the second data comprising said data indicative of the material distribution and geometry of a sample and determining a spectral profile for an XRD peak in an XRD response of the sample;
    a fitting module for analyzing said first and second data and the determined profile for the XRD peak, and optimizing a best match between the determined spectral profile and the first data, and
    a sample parameter calculator module for analyzing the best match data and determining the strain distribution of the sample.

8. A measurement system for measuring one or more parameters of a sample, the measurement system comprising:
    first and second units for providing first and second data comprising respectively X-ray Diffraction or High-Resolution X-ray Diffraction (XRD) response data of the sample indicative of a material distribution in the sample and optical response data of the sample to incident light indicative of at least a geometry of the sample; and
    the control system according to claim 1, configured for communicating with the first and second units and operable for processing and analyzing the first and second data for co-optimizing the first and second data, and utilizing the optimized data for determining said one or more parameters of the sample including a strain distribution in the sample.

9. The measurement system of claim 8, wherein the first unit comprises a measuring device for performing X-ray Diffraction or High-Resolution X-ray Diffraction measurement on the sample and providing said first data indicative of the material distribution in the sample.

10. The measurement system of claim 8, wherein the second unit comprises an optical measuring device for performing optical measurement on the sample and providing said second data indicative of the geometry of the sample.

11. The measurement system of claim 8, wherein at least one of the first and second units comprises a storage device for storing the at least one of the first and second data, and the other one of the first and second units comprises a measuring unit for performing measurements on the sample and providing the other one of the first and second data.

12. The measurement system of claim 8, wherein the first and second units are memory utilities of a storage system for storing the first and second data.

13. A method for use in measuring one or more parameters of a sample, the method comprising:
    providing first and second data comprising respectively X-ray Diffraction or High-Resolution X-ray Diffraction response data of the sample indicative of a material distribution in the sample and optical response data of the sample to incident light indicative of at least a geometry-related data of a sample, being either the same sample or a sample similar to said sample for which the XRD data is received; and
    utilizing the second data and processing and analyzing the first data for optimizing at least the first data, and utilizing the at least first optimized data for determining said one or more parameters of the sample including a strain distribution in the sample.

14. The method of claim 13, wherein said processing comprises combining the first and second data indicative of the material distribution in the sample and geometry of the sample for determining a spectral profile for an XRD peak, optimizing a best match between the determined spectral profile and the first data, and extracting optimal data for at least the strain distribution of the sample.

\* \* \* \* \*